United States Patent [19]

Gardner

[11] 4,153,617
[45] May 8, 1979

[54] ANOREXIC CHROMANS

[75] Inventor: Derek V. Gardner, Bishops Stortford, England

[73] Assignee: Beecham Group Limited, England

[21] Appl. No.: 849,948

[22] Filed: Nov. 9, 1977

Related U.S. Application Data

[60] Division of Ser. No. 652,041, Jan. 26, 1976, Pat. No. 4,080,335, which is a continuation-in-part of Ser. No. 599,694, Jul. 28, 1975, abandoned.

[30] Foreign Application Priority Data

Jul. 30, 1974 [GB] United Kingdom ............... 33549/74

[51] Int. Cl.$^2$ ............................................ C07D 311/02
[52] U.S. Cl. ..................................................... 260/345.2
[58] Field of Search ....................................... 260/345.2

[56] References Cited

FOREIGN PATENT DOCUMENTS 1357633  6/1974  United Kingdom ................... 260/345.2

Primary Examiner—Nicky Chan
Attorney, Agent, or Firm—Jacobs & Jacobs

[57] ABSTRACT

Compounds within formula

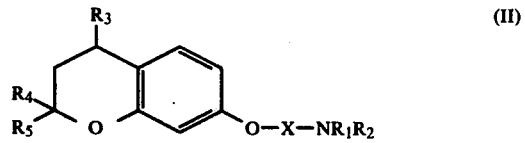

(II)

and their salts wherein X is alkylene of 2–4 carbon atoms; $R_1$ is hydrogen or alkyl of 1–6 carbon atoms; $R_2$ is hydrogen, alkyl of 1–6 carbon atoms or benzyl, or $R_1$ and $R_2$ together with the nitrogen atom to which they are attached form a 5-, 6- or 7- membered saturated ring; $R_3$ is aryl; $R_4$ is hydrogen or alkyl of 1–4 carbon atoms; and $R_5$ is hydrogen or alkyl of 1–4 carbon atoms; have been found to possess mood-modifying and anorexia inducing activity.

4 Claims, No Drawings

ANOREXIC CHROMANS

CROSS REFERENCE

This is a Divisional application of Ser. No. 652,041 filed Jan. 26, 1976, now U.S. Pat. No. 4,080,335, which is a continuation-in-part of Ser. No. 599,694, filed July 28, 1975, now abandoned.

BACKGROUND OF THE INVENTION

British Pat. No. 1,357,633 describes interalia compounds of the formula (I):

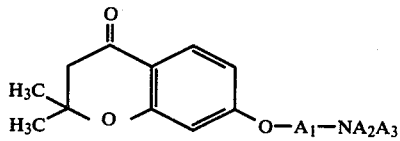

and salts thereof wherein $A_1$ is an alkylene group of 2–4 carbon atoms; $A_2$ is a hydrogen atom or a $C_{1-4}$ alkyl group and $A_3$ is a hydrogen atom or a $C_{1-4}$ alkyl group. These compounds were described as possessing activity on the central nervous system. However it is now believed that the compounds of the formula (I) are not sufficiently potent as use as anti-depressants. There has now been discovered a group of compounds which have more potent mood modifying activity than the compounds of the formula (I) and which at higher doses have the additional utility of suppressing appetite.

DESCRIPTION OF THE INVENTION

In one aspect the present invention provides compounds of the formula (II):

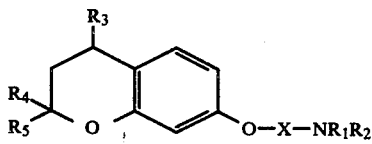

and salts thereof wherein X is an alkylene group of 2–4 carbon atoms; $R_1$ is a hydrogen atom or a $C_{1-6}$ alkyl group; $R_2$ is a hydrogen atom, a $C_{1-6}$ alkyl or benzyl group or $R_2$ is linked to $R_1$ so that the $NR_1R_2$ is a 5-, 6- or 7-membered saturated ring; $R_3$ is an aryl group; $R_4$ is a hydrogen atom or a $C_{1-4}$ alkyl group; and $R_5$ is a hydrogen atom or a $C_{1-4}$ alkyl group.

When used herein, the term 'aryl' means a phenyl, naphthyl, pyridyl, furyl, thienyl, pyrrolidyl, substituted phenyl or substituted naphthyl group. When used herein, the term 'substituted phenyl group' means a phenyl group substituted by one or two groups selected from fluorine, chlorine or bromine atoms or methoxyl, benzyloxyl, trifluoromethyl, methyl, nitro, acetoxyl, amino, methylamino, ethylamino, dimethylamino, diethylamino, acetamido, hydroxyl, methoxycarbonyl, ethoxycarbonyl, carboxamido, sulphonamido, nitrile, carboxy, trifluoromethoxy, trifluoromethylthio, methylsulphonyl, trifluromethylsulphonyl or methylthio group. When used herein, the term 'substituted naphthyl group' means a naphthyl group substituted by a fluorine, chlorine or bromine atom or by a methyl, methoxyl, trifluoromethyl, benzyloxy, hydroxyl, or methylthio group.

When used herein the term 'alkylene' means a straight or branched divalent alkyl group which produces a bridge of two or three carbon atoms between the O and N atoms.

Suitable groups $R_1$ include the hydrogen atom and the methyl, ethyl, propyl and butyl groups. Suitable groups $R_2$ include the hydrogen atom and the methyl, ethyl and benzyl groups. Suitable cyclic groups $NR_1R_2$ include pyrrolidino, piperidino, piperazinyl, N-methylpiperazinyl, morpholino and like groups.

Particularly suitable groups $NR_1R_2$ include the $NHCH_3$ and $N(CH_3)_2$ groups, the $N(CH_3)_2$ group being preferred.

Most suitably $R_4$ and $R_5$ are both methyl groups.

Suitable groups X include the $-CH_2.CH_2-$, $-CH_2.CH_2.CH_2-$, $-CH_2.CH(CH_3).CH_2-$ and $-CH_2.CH(CH_3)-$ groups. Most suitably X is a $-CH_2.CH_2-$ group.

One particularly suitable sub-group of compounds of the formula (II) are those of the formula (III):

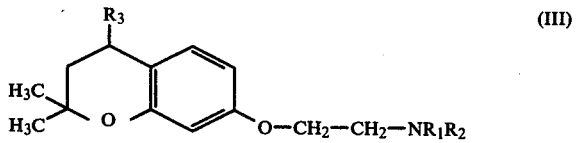

and salts thereof wherein $R_1$, $R_2$ and $R_3$ are as defined in relation to formula (II).

In the compounds of formula (III) $NR_1R_2$ is suitably a methylamino or dimethylamino group, the dimethylamino group being preferred.

Another particularly suitable group of compounds of formula (II) are those of the formula (IV):

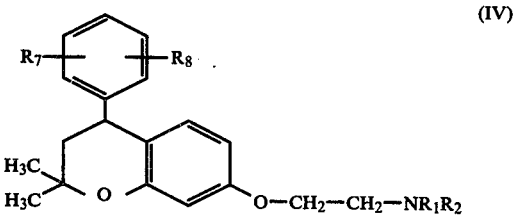

and salts thereof wherein $R_1$ and $R_2$ are as defined in relation to formula (II); $R_7$ is selected from a hydrogen, fluorine, chlorine or bromine atom or a trifluoromethyl, methyl, methoxy, nitro, cyano, hydroxyl, amino, dimethylamino, carboxamido, trifluoromethyloxy, trifluoromethylthio or sulphonamido group; and $R_8$ is a hydrogen, fluorine or chlorine atom or a trifluoromethyl, methoxyl, methyl or nitro group.

$R_7$ is most suitably a hydrogen, fluorine or chlorine atom or a methyl, methoxyl or trifluoromethyl group. $R_8$ is most suitably a hydrogen, fluorine or chlorine atom and is preferably a hydrogen atom.

Most suitably for the compounds of formula (IV) $R_1$ is a hydrogen atom or a methyl or ethyl group and $R_2$ is a methyl or ethyl group. Preferably both $R_1$ and $R_2$ are both methyl groups.

A further particularly suitable group of compounds of the formula (II) are those of the formula (V):

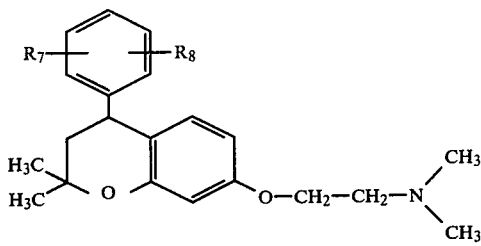

and salts thereof wherein suitable and preferred groups $R_7$ and $R_8$ are as defined in relation to formula (IV).

It is considered that compounds particularly worthy of mention include those of the formula (VI):

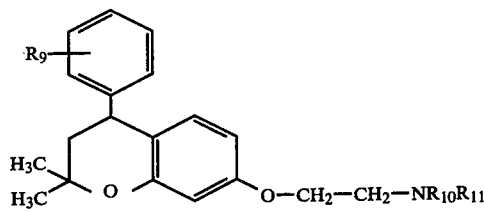

and salts thereof wherein $R_9$ is a hydrogen, fluorine, chlorine or bromine atom or a methyl, methoxyl or trifluoromethyl group; $R_{10}$ is a hydrogen atom or a methyl or ethyl group; and $R_{11}$ is a methyl or ethyl group or is joined to $R_{10}$ so that $NR_{10}R_{11}$ is a piperidino, pyrrolidino or morpholino group.

Most suitably $R_{11}$ is not joined to $R_{10}$.

In certain particularly suitable compounds of the formula (VI) $NR_{10}R_{11}$ is a methylamino group. In certain preferred compounds of the formula (VI) $NR_{10}R_{11}$ is a dimethylamino group.

Particularly favoured compounds of the formula (VI) include those wherein $R_9$ is a meta- or para- trifluoromethyl group.

A further particularly suitable group of compounds of this invention are those of the formula (VII):

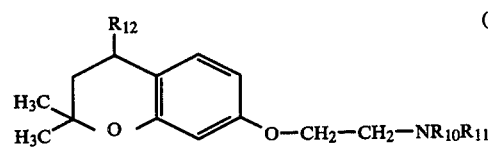

and salts thereof wherein $R_{10}$ and $R_{11}$ are as defined in relation to formula (VI) and $R_{12}$ is a naphthyl or substituted naphthyl group.

In certain particularly suitable compounds of the formula (VII) $NR_{10}R_{11}$ is a methylamino group. In certain preferred compounds of the formula (VII) $NR_{10}R_{11}$ is a dimethylamino group.

Most suitably $R_{12}$ is naphthyl and preferably a 2-naphthyl group.

Particularly favoured compounds according to this invention by virtue of their particularly acceptable separation of desirable anti-depressant and undesirable stimulant effects may be selected from:

(a) 2,2-dimethyl-7-(2-methylaminoethoxy)-4-(4-trifluoromethylphenyl)chroman (b) 2,2-dimethyl-7-(2-methylaminoethoxy)-4-(3-trifluoromethylphenyl)chroman (c) 2,2-dimethyl-7-(2-dimethylaminoethoxy)-4-(4-trifluoromethylphenyl)chroman (d) 2,2-dimethyl-7-(2-dimethylaminoethoxy)-4-(3-trifluoromethylphenyl)chroman (e) 2,2-dimethyl-7-(2-methylaminoethoxy)-4-(2-naphthyl)chroman (f) 2,2-dimethyl-7-(2-dimethylaminoethoxy)-4-(2-naphthyl)chroman and pharmaceutically acceptable salts thereof.

Since the compounds of this invention are nitrogenous bases they are able to form acid addition salts in conventional manner. Normally and preferably such salts are those formed from pharmaceutically acceptable organic or inorganic acids such as citric, acetic, propionic, lactic, tartaric, mandelic, succinic, fumaric, oleic, glutamic, gluconic, methanesulphonic, toluenesulphonic, sulphuric, phosphoric, hydrobromic, hydrochloric or the like acids. As will be recognized by those familiar with the formulation of pharmaceutical agents, the nature of the salting acid is relatively unimportant as long as it forms a stable and preferably crystalline pharmaceutically acceptable acid addition salts. Certain compounds within this invention and their salts are able to form solvates such as hydrates, for example, monohydrates.

Since the compounds of this invention contain an assymetric carbon atom at the 4-position of the chroman system they can exist as two optical isomers or mixtures of such isomers, for example racemic mixtures.

Compounds within the formula (II) affect the central nervous system. Thus depending on the dosage used, certain compounds of the formula (II) are able to produce anorexic or mood modifying effects in mammals.

Accordingly, in one of its aspects the present invention provides pharmaceutical compositions which comprise a compound of this invention as hereinbefore described together with a pharmaceutically acceptable carrier.

Normally, the compositions of this invention are adapted for oral administration to humans although compositions adapted for parenteral administration are also envisaged.

The most suitable dosage forms are unit dosage forms such as tablets, capsules, sachets and the like which contain a predetermined quantity of active material.

Such unit dosage forms normally contain from 0.1 to 200 mg of active material and may be taken once a day or several times a day according to the dose desired. Generally a human adult will be administered from 1 to 600 mgs per day, for example, from 5 to 200 mgs.

If the composition of this invention is intended for the induction of anorexia the composition will normally be in the form of a solid unit dosage form which contains from 1 mg to 200 mg of active ingredient, for example, 2 mg to 150 mg of active ingredient.

If the composition of this invention is intended for mood-modification such as anti-depressant effects, it is likely that it will be used as a solid unit dosage form which contains from 0.1 mg to 50 mg of active ingredient, for example, 1 mg to 25 mg of active ingredient.

In a further aspect this invention provides a method of suppressing appetite, which comprises administering an anorexically effective amount of a compound of this invention.

In a further aspect this invention provides a method of reducing depression, which comprises administering an anti-depressively effective amount of a compound of this invention.

The useful anorexic activity of compounds of this invention may be determined by the oral administration to hungry rats of the compound and measuring the reduction in their food intake. The results given in Table I were obtained for racemic compounds of the formula (VIII):

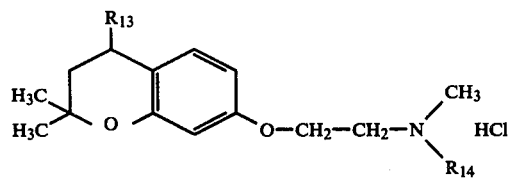

TABLE I
Anorexic Activity of Some Compounds of the Invention

| $R_{13}$ | $R_{14}$ | Approximate Dose Required to Reduce Food Intake by 50% (mg/kg) |
|---|---|---|
| 3-chlorophenyl | $CH_3$ | 5 |
| 4-chlorophenyl | $CH_3$ | 0.6 |
| 4-methoxyphenyl | $CH_3$ | 3 |
| 3-trifluoromethylphenyl | $CH_3$ | 23 |
| 4-trifluoromethylphenyl | $CH_3$ | 10 |
| phenyl | $CH_3$ | 4 |
| 4-trifluoromethylphenyl | H | 18 |
| 3-trifluoromethylphenyl | H | 32 |
| 1-naphthyl | $CH_3$ | 1.4 |
| fenfluramine | | 4 |
| diethylpropion | | 17 |

The useful mood-modifying activity of the compounds of this invention may be determined by standard tests such as the Reserpine Prevention test which demonstrates the ability of the compounds to prevent reserpine-induced hypothermia in mice. The results given in Table II were obtained for racemic compounds of the formula (IX):

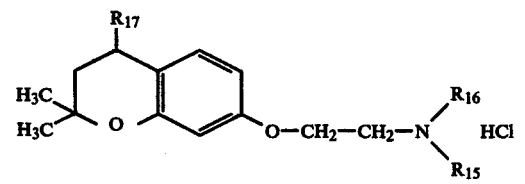

TABLE II
Dose at which Certain Compounds of the Invention are Active on the Reserpine Prevention Test

| $R_{15}$ | $R_{16}$ | $R_{17}$ | Approximate Dose Required (mg/kg) |
|---|---|---|---|
| $CH_3$ | $CH_3$ | 4-trifluoromethylphenyl | 10 |
| $CH_3$ | $CH_3$ | phenyl | 1 |
| $CH_3$ | $CH_3$ | 3-trifluoromethylphenyl | 0.3 |
| $C_2H_5$ | $C_2H_5$ | phenyl | 3 |
| $CH_3$ | $CH_3$ | 1-naphthyl | 3 |
| $CH_3$ | H | 2-naphthyl | 0.1 |
| amitriptyline | | | 3 |
| imipramine | | | 10 |

The D- and L-isomers of the compounds of this invention do not necessarily have identical pharmaceutical activity. Thus, for example, (−)-2,2-dimethyl-7-dimethylaminoethoxy-4-(3-trifluoromethylphenyl)-chroman is a more potent anorexiogenic agent and a more potent mood-modifying agent than the corresponding (+)-isomer. Thus, in many cases, those optical isomers of the compounds of the formula (II) which have the same stereochemistry at the 4-position of the chroman ring as (−)-2,2-dimethyl-7-dimethylaminoethoxy-4-(3-trifluoromethylphenyl)chroman are more suitable then the corresponding isomer which has the opposite stereochemistry at that point. Accordingly if one intends to use a single optical isomer of a compound of the formula (II) to reduce appetite or alleviate depression then that isomer should be that which has the same stereochemistry at the 4-position of the chroman ring as (−)-2,2-dimethyl-7-dimethylaminoethoxy-4-(3-trifluoromethylphenyl)chroman.

The present invention also describes the preparation of compounds of the formula (II) as hereinbefore defined which processes comprise:

(a) The reaction of a compound of the formula (X):

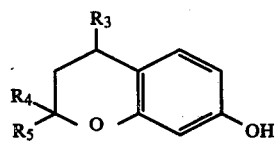

or a salt thereof wherein $R_3$, $R_4$ and $R_5$ are as defined in relation to formula (II), with either (i) a compound of the formula (XI):

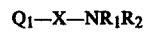

or a salt thereof wherein X, $R_1$ and $R_2$ are as defined in relation to formula (II) and $Q_1$ is a group readily displaceable by a nucleophile or (ii) a compound of the formula (XII):

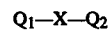

wherein $Q_1$ and X are as defined in relation to formula (XI) and $Q_2$ is a group readily displaceable by a nucleophile, so as to form a compound of the formula (XIII):

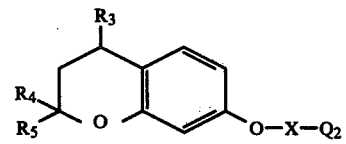

and thereafter reacting the compound of the formula (XIII) with an amine of the formula (XIV):

wherein $R_1$ and $R_2$ are as defined in relation to formula (II).

(b) The reaction of a compound of the formula (XV):

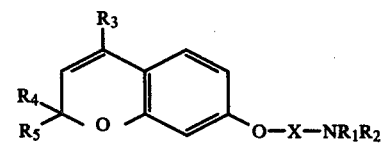

or a salt thereof wherein $R_1$, $R_2$, $R_3$, $R_4$, $R_5$ and X are as defined in relation to formula (II), with a reducing agent capable of reducing the vinylic double bond.

(c) The reaction of a compound of the formula (XVI):

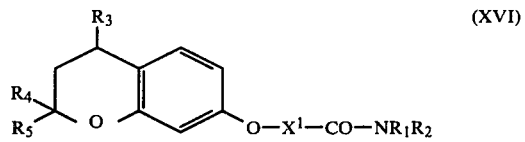

(XVI)

wherein $R_1$, $R_2$, $R_3$, $R_4$ and $R_5$ are as defined in relation to formula (II) and $X^1$ is a group such that $X^1$—$CH_2$ is a group X as defined in relation to formula (II), with a complex metal hydride capable of reducing amides to amines.

(d) For those compounds of the formula (II) wherein $R_1$ is a hydrogen atom, by the hydrogenation of the corresponding compound of the formula (II) wherein $R_1$ is a group removable by hydrogenolysis.

(e) For those compounds of the formula (II) wherein $R_1$ and/or $R_2$ are alkyl groups, by the alkylation of a corresponding compound of the formula (II) wherein $R_1$ is a hydrogen atom and $R_2$ is a hydrogen atom or alkyl group.

(f) For those compounds of the formula (II) wherein $R_4$ and $R_5$ are both methyl groups by the dehydration of a compound of the formula (XVII):

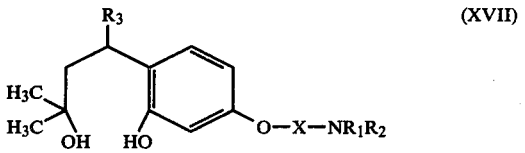

(XVII)

wherein $R_1$, $R_2$, $R_3$ and X are as defined in relation to formula (II).

(g) The reaction of a compound of the formula (XIII) as hereinbefore defined with an amine of the formula (XIV) as hereinbefore defined.

The reaction of a compound of the formula (X) or its anion with a compound of the formula (XI) is normally carried out in an inert solvent. Suitable solvents include hydrocarbons such as toluene or xylene, ethers such as dimethoxyethane or dimethoxypropane, ketones such as acetone, alcohols such as ethanol and other conventional solvents.

If desired the anion of the compound of the formula (X) may be produced before the etherification reaction or may be produced in situ by reaction with a base such as NaH or the like.

Generally any non-extreme temperature is used, but the reaction is substantially complete in a conveniently short time if an elevated temperature is used. For example, the reaction may be carried out at from about 0°–180° C., preferably in the region of 50°–120° C., for example, at about 70°–100° C.

Suitable groups $Q_1$ in the compound of the formula (XI) include conventional good leaving groups such as chlorine, bromine or iodine atoms or groups of the formula $O.SO_2R^1$ or $O.CO_2R^1$ where $R^1$ is an inert organic group such as a methyl, ethyl, phenyl, tolyl or like group. The group $Q_2$ in the compounds of formulae (XII) and (XIII) may also have these values.

The reaction of a compound of the formula (X) with one of the formula (XII) may take place under similar conditions to those outlined for the reaction of the compound of the formula (X) with one of the formula (XI).

The reaction of the compound of the formula (XIII) with an amine of the formula (XIV) will normally take place in an inert organic solvent such as a lower alkanol such as methanol, ethanol or the like or a halohydrocarbon such as methylene chloride or chloroform or the like. Such reactions take place at non-extreme temperatures such as −20°–140° C., and more usually at conventional temperatures such as 0°–30° C., for example at ambient temperature.

The reduction of the compound of the formula (XV) is normally brought about by catalytic hydrogenation. Such hydrogenation reactions will generally take place in organic solvents such as methanol, ethanol, methyl acetate, ethyl acetate or other conventional hydrogenation solvents using a low, ambient or elevated pressure of hydrogen. Generally from 1-5 atmospheres of hydrogen are used. Normally the reaction takes place at a non-extreme temperature such as 0°–100° C., for example 12°–80° C.

The catalyst used in these reactions will normally be a transition metal catalyst such as palladium. We have found 10-30% palladium on charcoal to be suitable.

The reduction of a compound of the formula (XVI) is normally effected using a complex hydride such as lithium aluminium hydride. Such reactions are carried out in an inert solvent medium such as dry ether solvent, for example, in tetrahydrofuran, dioxane, diethylether or the like. The reaction may be carried out at any non-extreme temperature, for example, 0°–120° C. and more suitably at an ambient or slightly elevated temperature, for example, at about 15°–80° C.

The compounds of the formula (II) wherein $R_1$ is a hydrogen atom are preparable from compounds of the formula (II) wherein $XNR_1R_2$ is a group $XNR_2R_{20}$ wherein $R_{20}$ is an optionally substituted benzyl group.

Such groups include the benzyl, benzhydride, trityl, methoxybenzyl, halobenzyl, dimethoxybenzhydride or other equivalent group. Normally the removal of this group is effected by catalytic hydrogenation, for example, using low, medium or high pressures of hydrogen over a transition metal catalyst. We have found 1-5 atmospheres of hydrogen to be suitable for use in conjunction with a palladium on charcoal catalyst. Normally the reaction is carried out at a non-extreme temperature such as 0°–100° C., for example, 12°–80° C.; in a conventional solvent such as methanol, ethanol, methyl acetate, ethyl acetate or the like.

The compounds of the formula (II) wherein $R_1$ and/or $R_2$ are alkyl groups may be prepared by conventional methods of alkylation from corresponding compounds. Reaction with compounds $R_1Q_1$ or $R_2Q_1$ under conventional conditions may be employed but in general are not preferred because they tend to lend to unacceptable side reactions. Particularly suitable methods of alkylation include reductive alkylation using an aldehyde in the presence of a reducing agent. For example, compounds of the formula (II) wherein $R_1$ and/or $R_2$ are methyl groups may be prepared by reaction with formaldehyde in the presence of formic acid or by reaction with formaldehyde in the presence of a reducing agent such as hydrogen and a transition metal catalyst. Such reactions normally take place at a non-extreme temperature such as −10°–120° C., for example, 10°–60° C. and preferably at ambient temperature. Such reaction frequently takes place in a conventional organic solvent.

Dehydration of the compounds of the formula (XVII) may be brought about by treatment with an acid catalyst and/or by heating. Generally the reaction takes place in a solvent which is frequently a hydrocarbon solvent. Suitable acid catalysts include mineral acids or stronger organic acids such as toluenesulphonic acid. If the dehydration is promoted by heating it is frequently sufficient to warm the reaction medium to 25°–100° C.

The reaction of a compound of the formula (XIII) with an amine (XIV) occurs under conventional conditions as hereinbefore described.

Intermediates of the formula (X) may be prepared by the detherification of a compound of the formula (XVIII):

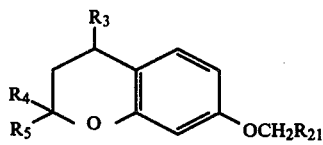

(XVIII)

wherein $R_{21}$ is a hydrogen atom or phenyl group.

Demethylation of such a compound may be brought about by the action of a strong acid such a hydroiodic acid or hydrobromic acid and debenzylation may be brought about by catalytic hydrogenation in conventional manner.

Compounds of the formula (XVIII) may be prepared by the hydrogenation of the corresponding compound of the formula (XIX):

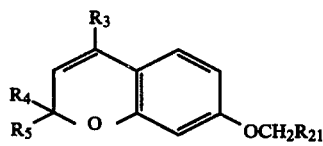

(XIX)

wherein $R_3$, $R_4$, $R_5$ and $R_{21}$ are as defined in relation to formula (II).

Such hydrogenation reactions may be carried out in ethanol at ambient temperature using hydrogen at atmospheric pressure and a 10% palladium on charcoal catalyst.

The compounds of the formula (XIX) may be prepared by the reaction of a compound of the formula (XX):

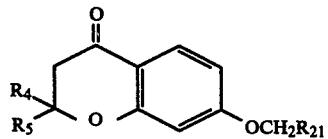

(XX)

wherein $R_4$, $R_5$ and $R_{21}$ are as defined in relation to formula (XIX) and a metal derivative of the formula $R_3M$ where M is Li, Na, MgI, MgBr or MgCl in conventional manner.

The compounds of the formula (XV) may be prepared by the reaction in a conventional manner of the corresponding compound of the formula (XXI):

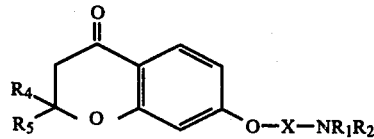

(XXI)

wherein $R_1$, $R_2$, $R_4$, $R_5$ and X are as defined in relation to formula (II) with a compound of the formula $R_3M$ where M is Li, Na, MgI, MgBr or MgCl, followed by dehydration.

The initial step of such reaction takes place in aprotic media, for example, in an ether solvent such as diethylether, tetrahydrofuran, dimethoxyethane or the like. The dehydration stage may conveniently be carried out using an aqueous or alkanolic solution of an acid in conventional manner.

The compound of the formula (XXI) may be prepared from the corresponding compound of the formula (XXII):

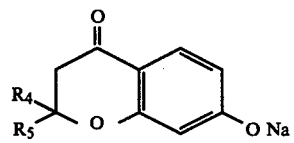

(XXII)

by conventional methods of ether formation such as by reaction of the sodium salt with a compound such as $Cl\text{—}X\text{—}NR_1R_2$ at ambient temperature in an alkanolic or similar solvent.

Compounds of the formula (XVII) may be prepared by the reaction of $CH_3Li$, $CH_3MgBr$, $CH_3MgI$, $CH_3MgCl$ or the chemical equivalent on a compound of the formula (XXIII):

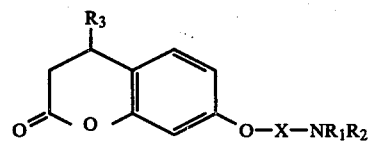

(XXIII)

wherein $R_1$, $R_2$, $R_3$ and X are as defined in relation to formula (II). Such reactions occur under conventional conditions for Grignard reactions, for example, in an ether solution in the absence of water. As previously indicated the resulting diol frequently dehydrates spontaneously during work up to yield a chroman of the formula (II), especially if heat or acid is involved in the work up.

Compounds of the formula (XXIII) may be prepared from the corresponding compound of the formula (XXIV):

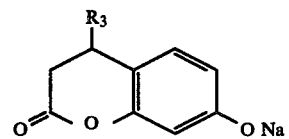

(XXIV)

with a compound such as $Cl\text{—}X\text{—}NR_1R_2$ at ambient temperature in an alkanolic or similar solvent.

Compounds of the formula (II) wherein $XNR_1R_2$ is a $CH_2CH_2NH_2$ group may also be prepared by a further process of the invention which comprises the reduction of a corresponding compound wherein the $XNR_1R_2$ group is a $CH_2CN$ group which compound in turn may be prepared from, for example, a sodium salt of a compound of the formula (X) and compound such as $BrCH_2CN$.

Compounds within the formula (II) which are optically pure at the 4-position may be prepared by the reaction of the corresponding resolved compound of the formula (X) as hereinbefore described with a compound of the formula (XI) as hereinbefore described. The appropriate resolved compound of the formula (X) may be prepared by the expulsion of the elements of carbon dioxide from a compound of the formula (XXV):

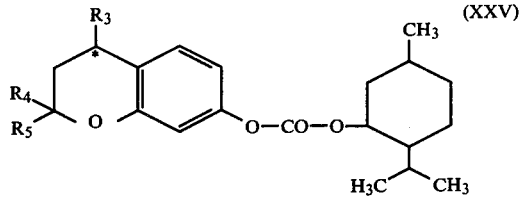

or an anlogue thereof wherein R₃, R₄ and R₅ are as defined for the compound of the formula (II) and the asterisk indicates that the compound is a substantially pure optical isomer at that carbon atom.

The elements of carbon dioxide may be generally removed from the compound of the formula (XXV) by heating to about 200° C. optionally in the presence of a high boiling inert solvent.

The carbonate of the formula (XXV) may be obtained by resolution of the corresponding racemate. Such resolution may be brought about by fractional crystallisation from solvents such as ethanol and ethanol/diethyl ether mixtures. The racematic carbonate may be prepared by the acylation of a compound of the formula (X) with (−)-menthyloxycarbonylchloride in ether solution in the presence of a tertiary base such as pyridine.

EXAMPLE 1

2,2-Dimethyl-7-dimethylaminoethyloxy-4-(3-trifluoromethylphenyl) chroman hydrochloride To a solution of 2,2-dimethyl-7-dimethylaminoethyloxy-4-(3-trifluoromethylphenyl)-2H- chromene hydrochloride (4.96 g) in ethanol (75 ml) was added 10% palladium on charcoal. The mixture was hydrogenated under hydrogen (1 atmosphere pressure) at ambient temperature (about 18° C.) until no further hydrogen was taken up. The mixture was filtered and the solvent removed from the resulting filtrate under reduced pressure to yield the title compound (3.7 g), m.p. 188°–190° C.

[2,2-Dimethyl-7-dimethylaminoethyloxy-4-(3-trifluoromethylphenyl)chroman and its pharmaceutically acceptable acid addition salts are highly favoured compounds of this invention].

EXAMPLE 2

Using a process strictly analogous to that of Example 1 compounds of the formula

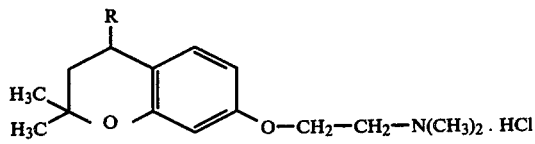

were prepared wherein R is as follows:

| R | m.p.(°C.) |
|---|---|
| 3-chlorophenyl | 158 |
| 4-chlorophenyl | 195–8 |
| 4-methoxyphenyl | 143–8 |
| 4-fluorophenyl | 156–8 |
| 4-methylphenyl | 201–2 |
| 4-trifluoromethylphenyl | 201–3 |
| 3-methoxyphenyl | 160 |
| 4-chloro-3-trifluoromethylphenyl | 211–2 |
| 2-methoxyphenyl | 211–3 |
| 4-fluoro-3-trifluoromethylphenyl | 196 |
| 2-naphthyl | 214.5–217.5 |
| 2-naphthyl | 198–200 (as ½ hydrate) |
| 2-furyl* | 188–193 (as ½ hydrate) |
| 3,5-bistrifluoromethylphenyl | 174–6 |
| 2-methylphenyl | 181–3 |
| phenyl | 165–7 |

(*catalyst used was platinum on charcoal).
(**recrystallised from ethyl acetate).
(***recrystallised from acetone/ethanol)

EXAMPLE 3

2,2-Dimethyl-7-(2-dimethylaminoethoxy)-4-(1-naphthyl)chroman

To a stirred solution of 2,2-dimethyl-4-(1-naphthyl)-7-chromanol (7.48 g) in dry toluene (50 ml) was added sodium hydride (1.5 g, ~1.5 eq., 60% dispersion in oil) and the mixture was brought to reflux. To the resulting solution was added dropwise over 10 minutes a solution of 2-dimethylaminoethyl chloride (2.70 g, ~1.1 eq.) in dry toluene (10 ml) and the mixture was stirred under reflux for 2 hours, cooled, diluted with water and left to stand overnight. Next day the toluene layer was separated and evaporated in vacuo. The aqueous layer was extracted with ether and the extract used to dissolve the residue from the toluene evaporation. The organic layer was extracted with 5 N hydrochloric acid (45, 35 and 20 ml respectively), the combined acid extract was basified and extracted into ether. After being dried the ether was removed in vacuo to give a yellow oil (6.2 g) which was chromatographed on alumina in 8% ether–92% petroleum ether (b.p. 60–80) to give the title compound (4.71 g, 51%) as a colourless oil. The hydrochloric salt had m.p. 178.5°–181.5° C.

EXAMPLE 4

2,2-Dimethyl-7-methylaminoethoxy-4-(4-trifluoromethylphenyl)chroman hydrochloride 7-(N-Benzyl-N-methylaminoethoxy)-2,2-dimethyl-4-(trifluoromethylphenyl)-2H-chromene hydrochloride (5.9 g) was dissolved in ethanol (100 ml) containing glacial acetic acid (3 drops). 10% Pd/C (0.6 g) was added and the mixture hydrogenated at ambient temperature (about 18° C.) under 6 atmospheres of hydrogen until no further hydrogen was taken up. The resulting mixture was filtered and the solvent removed under reduced pressure to yield the title compound (3 g), m.p. 178°–180° C. (ex-acetone).

A strictly analogous procedure led to the production of 2,2-dimethyl-7-methylaminoethyloxy-4-(3-trifluoromethylphenyl)chroman hydrochloride, m.p. 182°–184° C., to 2,2-dimethyl-7-methylaminoethoxyloxy-4-(4-fluorophenyl)chroman hydrochloride, m.p. 222°–224° C., to 2,2-dimethyl-7-methylaminoethyloxy-4-phenylchroman hydrochloride, m.p. 191°–193° C., and to 2,2-dimethyl-7-dimethylaminoethoxy-4-(3-fluorophenyl)chroman hydrochloride, m.p. 168°–171.5° C.

[2,2-Dimethyl-7-methylaminoethoxy-4-(4-trifluoromethylphenyl)chroman and 2,2-dimethyl-7-methylaminoethoxy-(3-trifluoromethylphenyl)chroman and their pharmaceutically acceptable salts are particularly favoured compounds of this invention].

EXAMPLE 5

7-N-Benzylmethylaminoethyloxy-2,2-dimethyl-4-(3-trifluoromethylphenyl)chroman hydrochloride N-benzylmethylaminoethyl chloride hydrochloride (1.37 g) was added to 2,2-dimethyl-4-(3-trifluoromethylphenyl)chroman-7-ol (2.0 g), potassium carbonate (5.16 g) and potassium iodide (1.03 g) in methyl ethyl ketone (50 ml). The mixture was refluxed for 2 days and left to stand at ambient temperature for a further 3 days. The mixture was filtered and the solvent evaporated under reduced pressure. The resulting crude oil was taken up in water, and extracted into ether. The ether was dried (MgSO4) and the solvent was evaporated under reduced pressure to yield an oil. This oil was dissolved in dry ether and passage of dry hydrogen chloride through the solution yielded the title compound (1.0 g) as a non-crystalline foam which analysed as the monohydrate.

EXAMPLE 6

2,2-Dimethyl-7-dimethylaminoethyloxy-4-(-4-trifluoromethylphenyl)chroman hydrochloride Dimethylaminoethylchloride hydrochloride (1.5 g) was added to 2,2-dimethyl-4-(4-trifluoromethylphenyl)chroman-7-ol (1.0 g), potassium carbonate (4.0 g) and potassium iodide (1.5 g) in acetone (50 ml) and the mixture refluxed for 2 days. The mixture was filtered and the acetone was evaporated under reduced pressure. The resulting crude oil was chromatographed on alumina. Elution with ether:petrol (1:1) gave a clear oil which after dissolution in dry ether and passage of dry hydrogen chloride through the solution yielded the required chroman as the hydrochloride salt (0.35 g), m.p. 200°–203° C.

[2,2-Dimethyl-7-dimethylaminoethyloxy-4-(4-trifluoromethylphenyl)chroman and its pharmaceutically acceptable acid addition salts are highly favoured compounds of this invention].

A strictly analogous procedure led to the preparation of 7-(N-benzyl-N-methylaminoethyloxy)-2,2-dimethyl-4-(3-trifluoromethylphenyl)-2H-chromene hydrochloride, m.p. 138°–140° C.

EXAMPLE 7

2,2-Dimethyl-7-dimethylaminolethyloxy-4-(2-thienyl)-chroman hydrochloride

Sodium hydride (0.2 g of a 60% dispersion in oil) was added to 2,2-dimethyl-4-(2-thienyl)chroman-ol (0.1 g) in dry toluene (20 ml). The solution was stirred for 10 minutes. Dimethylaminoethyl chloride (0.5 g) was added and the solution was refluxed for 3 hr. The solvent was evaporated under reduced pressure. The oil was taken up in water and ether, the aqueous layer extracted with ether and the organic layers dried over magnesium sulphate. Removal of the solvent under reduced pressure gave a yellow oil. Dissolution in dry ether and passage of dry hydrogen chloride through the solution gave the required chroman as the hydrochloride salt (0.8 g, 57%), m.p. 120°–123° C., (ethyl acetate).

EXAMPLE 8

2,2-Dimethyl-7-dimethylaminoethoxy-4-phenyl chroman hydrochloride

A mixture of 2,2-dimethyl-7-hydroxy-4-phenylchroman (3.72 g), sodium hydride (0.53 g, 60% dispersion in oil) and 2-dimethylaminoethyl chloride (1.58 g) in toluene (59 ml) was stirred and boiled under reflux for 6 hours. Water was added to the cooled mixture and the organic layer was separated and extracted with 5 N hydrochloric acid (3×30 ml). The combined acid extract was basified, extracted with ether and the ether extract dried (magnesium sulphate). Removal of the solvent gave 2,2-dimethyl-7-dimethylaminoethoxy-4-phenylchroman which was isolated as its hydrochloride salt, m.p. 165°–167° C.

Analagous procedures were used to prepare compounds of the formula:

| $NR_1R_2$ | $R_3$ | $R_4$ | $R_5$ | X | m.p.° C. |
|---|---|---|---|---|---|
| $N(C_2H_5)_2$ | phenyl | $CH_3$ | $CH_3$ | $CH_2CH_2$ | 139–140 |
| $N(CH_3)_2$ | 3-trifluoromethylphenyl | $CH_3$ | $C_2H_5$ | $CH_2CH_2$ | 220–221.5 |
| $N(CH_3)_2$ | 3-trifluoromethylphenyl | $CH_3$ | $CH_3$ | $CH_2CH_2$ | 188–190 |
| morpholino | phenyl | $CH_3$ | $CH_3$ | $CH_2CH_2$ | 187 |
| pyrrolidino | phenyl | $CH_3$ | $CH_3$ | $CH_2CH_2$ | 162–164 |
| piperidino | phenyl | $CH_3$ | $CH_3$ | $CH_2CH_2$ | 191 |
| $NH(CH_3)$ | phenyl | $CH_3$ | $CH_3$ | $CH_2CH(CH_3)$ | 124 |
| $N(CH_3)_2$ | phenyl | $CH_3$ | $CH_3$ | $(CH_2)_3$ | 145–147 |
| $N(CH_3)_2$* | phenyl | $C_2H_5$ | $C_2H_5$ | $CH_2CH_2$ | 168–177 |

*This compound was prepared as its hydrobromide salt

EXAMPLE 9

2,2-Dimethyl-7-dimethylaminoethoxy-4(4-trifluoromethylphenyl)chroman hydrochloride 2,2-Dimethyl-7-(2-hydroxyethoxy)-4-(-4-trifluoromethylphenyl)chroman tosylate (0.65 g) was dissolved in a solution of dimethylamine (excess) containing a trace of sodium iodide and the mixture was heated in an autoclave at 120° C. for four hours and allowed to cool to room temperature overnight. The solvents were then removed under reduced pressure. The resulting dark oily solid was washed with dilute sodium bicarbonate and taken up into ether. The ether solution was dried (MgSO4) and the solvent evaporated under reduced pressure to yield an oil. The oil was redissolved in dry ether and the passage of dry hyrdogen chloride through the solution yielded the title compound.

EXAMPLE 10

2,2-Dimethyl-7-(2-dimethylamino-2-propyloxy)-4-phenylchroman hydrobromide

Sodium hydride (0.7 g of an 80% dispersion in oil) was added to a solution of 2,2-dimethyl-4-phenyl chroman-7-ol (4.3 g) in dry toluene (30 ml). Ethyl-2-bromopropionate (3.1 g) was added and the solution refluxed for 18 hours. The solvent was evaporated under reduced pressure, the residue poured into water and extracted with ether. The ether layers were dried (MgSO4). Removal of the solvent under reduced pressure gave an oil (5.5 g) which was chromatographed on alumina. Elution with ether:petrol (1:9) gave a colourless oil (1 g) whose spectroscopic properties were consistant with 2,2-dimethyl-7-(ethyl-2-oxypropionate)-4-phenylchroman. This was dissolved in ethanol (30 ml) and a 33% solution of dimethylamine in ethanol (20 ml) added. The reaction mixture was heated at 120° for 7 hours. Removal of the solvent under reduced pressure gave an oil which was chromatographed on alumina (100 g). Elution with ether:petrol (1:1) gave a yellow oil (0.3 g) whose spectroscopic properties were consistent with 2,2-dimethyl-7-(2-oxypropionamide)-4-phenylchroman. The amide (0.17 g) was dissolved in dry ether and lithium aluminium hydride (0.4 g) added. The mixture was filtered, washed with ether and the filtrate dried (MgSO4). Removal of the solvent under reduced pressure gave a clear oil which on dissolution in ether and passage of hydrogen bromide through the solution gave the required chroman hydrobromide (0.09 g) m.p. 122°–129° (after initial softening at 114°).

EXAMPLE 11

2,2-Dimethyl-7-dimethylaminoethoxy-4-(4-trifluoromethylphenyl)chroman

The title compound may be prepared by the method of R. N. Icke, V. B. Wisegarber and G. A. Alles, Organic Synthesis, Collected Volume 3, page 723 from 2,2-dimethyl-7-methylaminoethoxy-4-(4-trifluoromethylphenyl)chroman or from 2,2-dimethyl-7-aminoethoxy-4-(4-trifluoromethylphenyl)chroman. The corresponding 4-(3-trifluoromethylphenyl) compound may be prepared in an analogous manner.

2,2-Dimethyl-7-dimethylaminoethoxy-4-(3-trifluoromethylphenyl)chroman

Formaldehyde (30 ml of a 35% aqueous solution) was added to 7-aminoethyloxy-2,2-dimethyl-4-(3-trifluoromethylphenyl)chroman (1 g) in ethanol (30 ml) and the mixture was hydrogenated over 10% palladium of charcoal (0.1 g) at 4 atmospheres. The catalyst was removed by filtration and the filtrate evaporated under reduced pressure to give an oil which was taken up in water and extracted with ether. The ethereal extracts were evaporated to give an oil which contained the title compound.

EXAMPLE 12

2,2-Dimethyl-7-methylaminoethoxy-4-(4-trifluoromethylphenyl)chroman hydrochloride 7-(N-Benzyl-N-methylaminoethoxy)-2,2-dimethyl-4-(trifluoromethylphenyl)chroman hydrochloride (6 g) was hydrogenated as described in Example 4 to yield the title compound (3 g), m.p. 178°–180° C. (ex-acetone).

A strictly analogous procedure led to the production of the corresponding 4-(3-trifluoromethylphenyl) compound, m.p. 182°–184° C.

The above reactions may also be carried out using starting compounds in which the N-benzyl group is replaced by a N-(4-methoxybenzyl) or N-(4-chlorobenzyl) group.

EXAMPLE 13

(+)-2,2-Dimethyl-7-(2-dimethylaminoethoxy)-4-(3-triflfuoromethylphenyl)chroman hydrochloride

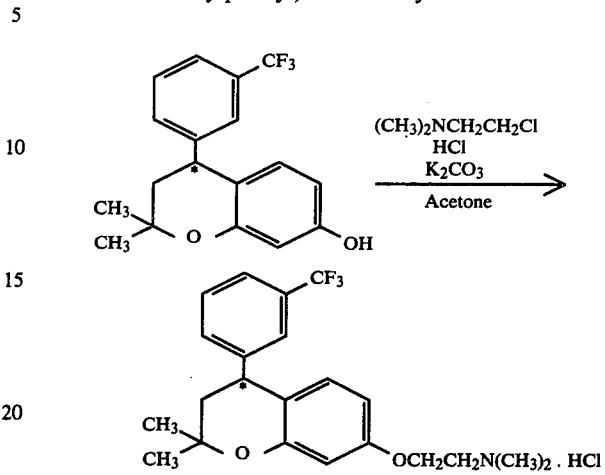

(+)-2,2-Dimethyl-4-(3-triflfuoromethylphenyl)chroman-7-ol (3.8 g) potassium carbonate (10 g) and dimethylaminoethyl chloride hydrochloride (4 g) refluxed in dry acetone (200 ml) for 16 hours, the solid filtered off and the acetone evaporated, giving a clear brown oil (3.6 g). This was dissolved in ether (100 ml), washed with water (100 ml) and the ether extracted with dilute HCl (2×50 ml, 5 N). The acid layer was neutralised (K2CO3) and extracted with ether (2×100 ml). The combined ether extracts were washed with water (2×50 ml) and evaporated, yielding a brown oil, α=+8.5 (3.3 g).

This was dissolved in chloroform and ethereal HCl added. The solid which separated was re-crystallised from chloroform/ether, yielding (+)-2,2-dimethyl-7-(2-dimethylaminoethoxy)4-(3-trifluoromethylphenyl)-chroman hydrochloride, m.p. 181° C., [α]=+8.5 (1.6 g).

In a similar manner, the (−)-chromanol yielded the (−)-chroman hydrochloride, m.p. 181° C., [α]=−10°.

A mixed melting point yielded a temperature range of 175°–195° C. Authentic unresolved material has a melting point of 180°–195° C. The n.m.r. spectra were identical with unresolved material.

EXAMPLE 14

2,2-Dimethyl-7-(2-dimethylaminoethoxy)-4-(6-methoxy-2-naphthyl)chroman hydrochloride Hydrogenation of 2,2-dimethyl-7-dimethylaminoethyl-4-(6-methoxy-2-naphthyl)-2H-chromene (6.2 g, 0.015 mole) with 10% palladium on carbon (600 mg) in ethanol (100 ml) gave, after removal of solvent, a quantitative yield of 2,2-dimethyl-7-(2-dimethylaminoethoxy)-4-(6-methoxy-2-naphthyl)chroman as a white crystalline solid which was converted to the hydrochloride salt, m.p. 175°–177° C.

EXAMPLE 15

2,2-Dimethyl-4-(2-naphthyl)-7-[2-(1-piperidino)ethoxy]chroman

Hydrogenation of 2,2-dimethyl-4-(2-naphthyl)-7-[2-(1-piperidino)ethoxy]-2H-chromene by a strictly analogous method to that described in Example 14 gave the title compound as a colourless oil.

2,2-Dimethyl-7-(2-methylaminoethoxy)-4-(2-naphthyl)chroman and 7-(2-diethylaminoethoxy)-2,2-dimethyl-4-(2-naphthyl)chroman were prepared from 7-[2-(N-benzyl-N-methylamino)ethoxy]-2,2-dimethyl-4-(2-naphthyl)-2H-chromene and 7-(2-diethylaminoethoxy)-2,2-dimethyl-4-(2-naphthyl)-2H-chromene respectively in a similar manner as colourless oils.

EXAMPLE 16

7-Aminoethyloxy-2,2-dimethyl-4-(3-trifluoromethylphenyl) chroman hydrobromide A solution of 7-cyanomethyloxy-2,2-dimethyl-4-(3-trifluoromethylphenyl) chroman (5.4 g) and 10% palladium on charcoal (0.5 g) in ethanol (75 ml) was hydrogenated at atmospheric pressure. The catalyst was removed by filtration and the filtrate evaporated under reduced pressure to give an oil which was treated with ethereal hydrogen bromide to give the title compound (4 g) as a very hygroscopic non-crystalline compound.

PREPARATION 1

2,2-Dimethyl-4-(3-trifluoromethylphenyl)chroman-7-ol

7-Benzyloxy-2,2-dimethyl-4-(3-trifluoromethylphenyl)-2H-chromene (10.0 g) was dissolved in ethanol (100 ml) and 10% Pd/C (1 g) added. This was hydrogenated at 60° and 5 atmospheres pressure for 18 hours. Filtration through kieselguhr and evaporation of the solvent under reduced pressure gave an oil which solidified on addition of carbon tetrachloride. Recrystallisation from carbon tetrachloride gave the title compound (7.7 g), m.p. 63°–68° C., (analysing as compound plus 1 mole of carbon tetrachloride).

An analogous procedure was used to prepare 2,2-dimethyl-4-phenyl-2H-chroman-7-ol, m.p. 103°–109° C. (ex ether-petrol).

An analogous procedure in which the reduction was carried out at 18° C. at atmospheric pressure yielded 2,2-dimethyl-4-(4-trifluoromethylphenyl)chroman-7-ol.

PREPARATION 2

7-Benzyloxy-2,2-dimethyl-4-(4-trifluoromethylphenyl)-2H-chromene n-Butyl-lithium (142 ml of a 2.4 M solution) was added under dry nitrogen to a solution of 4-bromobenzotrifluoride (76.5 g) in dry ether at −50° C. The mixture was left to stir for 2 hours. 7-Benzyloxy-2,2-dimethylchroman-4-one (64 g) in dry ether was added dropwise. Water was added and the ether layer washed with 5 N.HCl (2×100 ml), and dried (MgSO4). Removal of the solvent under reduced pressure gave an oil (84 g) which was chromatographed on alumina. Elution with petrol-ether (1:1) gave the title compound (52 g).

PREPARATION 3

2,2-Dimethyl-4-phenyl-2H-chromene-7-ol

Bromobenzene (141.3 g) in dry tethydrofuran (300 ml) was added to magnesium (23.7 g) in dry tetrahydrofuran (100 ml). 2,2-Dimethylchroman-4-one-7-ol (34.5 g) in dry tetrahydrofuran (250 ml) was then added and the solution refluxed for 48 hours. The mixture was poured into ammonium chloride solution, the tetrahydrofuran layer was separated and evaporated under reduced pressure. The aqueous layer was extracted with ethyl acetate and the organic layer and the residue from the tetrahydrofuran layer was shaken with 10% sodium hydroxide solution. The basic layer was acidified and re-extracted with ethyl acetate. The organic layers were dried (MgSO4). Removal of the solvent under reduced pressure gave an oil (26 g) which was chromatographed on silica. Elution with ether-petrol (1:1) gave the title compound (14 g).

PREPARATION 4

2,2-Dimethyl-4-(3-trifluoromethylphenyl)-2H-chromene-7-ol

3-Bromobenzotrifluoride (61 g) in dry ether (100 ml) was added to magnesium (6.6 g) in ether (50 ml). 2,2-Dimethylchroman-4-one-7-ol (17.4 g) suspended in ether (500 ml) was added and the mixture refluxed for 16 hourss. The reaction mixture was poured into ammonium chloride solution and extracted with ether. The combined ether layers were washed with 2 N HCl (2×100 ml) and dried (MgSO4). Removal of the solvent under reduced pressure gave the title compound (25 g), m.p. 102°–106° C.

PREPARATION 5

2,2-Dimethyl-7-dimethylaminoethyloxy-4-(3-trifluoromethylphenyl)-2H-chromene hydrochloride 4-Bromobenzotrifluoramide (38.4 g) in dry ether (70 ml) was added dropwise to magnesium (4.16 g) in dry ether (30 ml). The Grignard reagent was stirred and refluxed for ½ hr. after addition to the halide. 2,2-Dimethyl-7-dimethylaminoethyloxychroman-4-one (15.0 g) in dry ether (150 ml) was added dropwise. The mixture was poured into ammonium chloride solution and extracted with ether. The etheral layers were combined and washed with 5 N.HCl (3×100 ml). The acid layers were combined, basified and extracted with ether. The ether layers were dried (MgSO4). Removal of the solvent under reduced pressure gave an oil which was chromatographed on alumina (600 g). Elution with ether:petrol (1:1) gave a white solid (16.0 g). Dissolution in dry ether and passage of dry hydrogen chloride through the solution gave the required chromene as the hydrochloride salt (15.7 g) m.p. 181°–184° C.

The following compounds were prepared using the same method.

| R | m.p. °C. |
|---|---|
| phenyl | 186°–187° |
| 3-chlorophenyl | 193° |
| 4-chlorophenyl | 187°–190° |
| 4-methoxyphenyl | 171° |
| 4-fluorophenyl | 154° |
| 1-naphthyl | 192°–4° |
| 4-methylphenyl | 161° |
| 2-methoxyphenyl | 191°–3° |
| 2-naphthyl | 181.5°–183.5° |
| 3-thienyl | 203°–6° |
| 3-methoxyphenyl | 146° |
| 2-methylphenyl | 212–4° |
| 4-fluoro-3-trifluoromethylphenyl | |
| 4-chloro-3-trifluoromethylphenyl | 207° |

Also prepared by this method were 7-(N-benzylmethylaminoethyloxy)-2,2-dimethyl-4-(4-trifluoromethylphenyl)-2H-chromene hydrochloride m.p. 170°–174° and 7-(N-benzylmethylaminoethyl)-2,2-dimethyl-4-(3-trifluoromethylphenyl)-2H-chromene hydrochloride m.p. 138°-140°.

PREPARATION 6

4-Benzylideno-2,2-dimethyl-7-dimethylaminoethyloxy-chroman hydrochloride

Benzyl bromide (27 g) in dry ether was added dropwise to magnesium (2.8 g) in dry ether. The solution was refluxed for ½ hr. 2,2-dimethyl-7-dimethylaminoethyloxy chroman-4-one (15.0 g) in ether was added dropwise and the mixture refluxed 1 hour. The reaction mixture was worked up in the conventional manner to give the benzylideno-chroman hydrochloride (10.6 g), m.p. 224°-225° (ethanol) containing less than 10% of the 2H chromene isomer.

Similarly prepared were 2,2-dimethyl-7-dimethylaminoethyloxy-4-(3-trifluoromethylbenzylideno)-chroman hydrochloride which was obtained as an 87% pure isomer after fractional recrystallization from ethyl acetate; and 2,2-dimethyl-7-diemethylaminoethyloxy-4-(3-trifluoromethylbenzyl)-2H-chromene hydrochloride also 87% pure after fractional recrystallisation from ethyl acetate.

PREPARATION 7

4-(4-Bromophenyl)-2,2-dimethyl-7-dimethylaminoethyloxy-2H-chromene hydrochloride n-Butyl-lithium (28.6 ml of a 2.4 M solution) was added dropwise under dry nitrogen to a solution of dibromobenzene (13.5 g) in dry ether at −30° C., 2,2-dimethyl-7-dimethylaminoethyloxychroman-4-one (10.0 g) in dry ether was added dropwise and the solution was allowed to stir for 2 hours and then left to stand for 16 hours. Water (50 ml) was added and the mixture was extracted with 5 N.HCl (3×100 ml). The acid layers were basified, the basic solution extracted with ether and the ether layers dried (MgSO₄). Removal of the solvent under reduced pressure gave an orange oil (14 g) which was chromatographed on alumina (420 g). Elution with petrol - ether (1:1) gave the required chromene (9.1 g). Dissolution of this in dry ether and passage of hydrogen chloride through the solution gave the title compound (9.35 g), m.p. 182°-186° C. (ex acetone).

Similarly prepared were

| R | |
|---|---|
| | m.p. °C. |
| 4-trifluoromethylphenyl | 197°-199° |
| 3,5-bistrifluoromethylphenyl | sublimes from 154° |
| 2-trifluoromethylphenyl | 198°-200° |

PREPARATION 8

2,2-Dimethyl-7-dimethylaminoethyloxy-4-(2-furyl)-2H-chromene hydrochloride n-Butyl-lithium (56 ml of a 2 N solution) was added under dry nitrogen to a solution of furan (10 ml) in dry ether (15 ml) at room temperature and the solution was refluxed for 1 hour. 2,2-Dimethyl-7-dimethylaminoethyl oxychroman-4-one (10.0 g) in dry ether (40 ml) was added dropwise and the solution was refluxed for 1 hour. Water (50 ml) was added and the mixture extracted with 2 N.HCl (3×100 ml). The acid layers were basified and the basic solution extracted with ether and the organic layers dried (MgSO₄). Removal of the solvent under reduced pressure gave an oil (12.5 g) which was chromatographed on alumina (375 g). Elution with ether:petrol (1:1) gave an oil (11.5 g) which on dissolution in dry ether and passage of hydrogen chloride through the solution gave the title compound as the hydrochloride salt (8 g), m.p. 189°-191° C. (ex-ethyl acetate).

PREPARATION 9

2,2-Dimethyl-7-(2-dimethylaminoethoxy)-4-phenyl-2H-chromene

To a stirred solution of phenylmagnesium bromide [from bromobenzene and magnesium in dry tetrahydrofuran] was added 2,2-dimethyl-7-(2-dimethylaminoethoxy)-chroman-4-one in dry THF and the resulting solution was boiled under reflux for 2 weeks. The cooled reaction mixture was decomposed with 2.5 N hydrochloric acid and the organic layer separated and dried (magnesium sulphate). Removal of the solvent gave a yellow oil which was chromatograhed on silica in 3% ether–97% light petroleum (b.p. 60°-80°) gave the title compound as a colourless oil. Dissolution in dry ether and passage of dry hydrogen chloride through the solution gave the hydrochloride salt, m.p. 186.5°-187.5°. An analogous procedure yielded 7-(2-N-benzyl-N-methyl-aminoethoxy)-4-(4-fluorophenyl)-2,2-dimethyl-2H-chromene as a colourless oil.

PREPARATION 10

2,2-Dimethyl-4-(2-thienyl)chroman-7-ol (a) 7-Hydroxy-4-(2-thienyl) dihydrocoumarin 2-Thienylacrylic acid (5 g) and resorcinol (3.6 g) were dissolved in concentrated hydrochloric acid (100 ml) and the mixture refluxed for 1 hour with passage of gaseous hydrogen chloride through the reaction mixture. The hydrochloric acid was decanted off and the residue washed with saturated sodium bicarbonate solution. Filtration afforded the dihydrocoumarin as a buff-coloured solid (6.72 g).

(b) 2,2-Dimethyl-4-(2-thienyl)chroman-7-ol

Methyl-lithium (150 ml of a 2 N solution) was added under dry N₂ to a solution of 7-hydroxy-4-(2-thienyl) dihydrocoumarin (14.8 g) in dry ether (120 ml) and the mixture allowed to stand for 3 days. Water (500 ml) was added and the ether layer discarded. The aqueous layer was acidified, extracted with ether and the combined ether layers dried (MgSO₄). Removal of the solvent under reduced pressure gave a black oil which was then dissolved in dry benzene (100 ml) containing a trace of p-toluene sulphonic acid. The mixture was heated under reflux for 3 hours in a Dean & Stark apparatus. Removal of the solvent under reduced pressure and chromatography on silica gave the required phenol (7 g).

PREPARATION 11

7-(N-Benzyl-N-methylaminoethyloxy)-2,2 dimethylchroman-4-one

N-Benzylmethylaminoethylchloride hydrochloride (14.98 g) was added to a mixture of potassium carbonate (86.28 g), potassium iodide (17.28 g) and 2,2-dimethylchroman-4-one-7-ol (20 g) and the reaction mixture refluxed in acetone for two days. Filtration and removal of the solvent under reduced pressure gave an oil which was taken up in ether and washed with 1 M sodium hydroxide and then with water. The ether layer was dried (MgSO$_4$) and evaporated under reduced pressure to give the title compound as an oil (19.9 g).

PREPARATION 12

2-Ethyl-4-(3-trifluoromethylphenyl)-7-hydroxy-2-methylchroman (a)

2-Ethyl-4-(3-trifluoromethylphenyl)-7-hydroxy-2-methyl-2H-chromene

2-Ethyl-7-hydroxy-2-methyl-4-chromanone, m.p. 109°–110.5° C., was prepared by condensing resorcinol with 3-methyl-2-pentanoic acid in the presence of boron trifluoride diethyl etherate. Reaction of the chromanone with 3-trifluoromethylphenyl magnesium bromide as described in Preparation 5 gave the title chromene as a golden yellow oil.

(b)

2-Ethyl-4-(3-trifluoromethylphenyl)-7-hydroxy-2-methylchroman

A solution of the chromene in ethanol was hydrogenated at atmospheric pressure and ambient temperature in the presence of 10% palladium on charcoal. When hydrogen uptake had ceased the catalyst was removed by filtration through kieselguhr and the resulting filtrate was evaporated in vacuo to give the title chroman as a pale yellow oil.

PREPARATION 13

2,2-Dimethyl-7-(2-dimethylaminoethoxy)-4-(1-naphthyl)chroman hydrochloride (a) 3,4-Dihydro-7-hydroxy-4-(1-naphthyl)coumarin Condensation of resorcinol with 3-(1-naphthyl)acrylic acid in the presence of hydrochloric acid/hydrogen chloride (method of J. D. Simpson and H. Stephen, J. Chem. Soc. (London) 1936, 1382) gave the desired dihydrocoumarin, m.p. 203.5–206.5, in 64% yield.

(b) 2,2-Dimethyl-4-(1-naphthyl)-7-chromanol

To a stirred solution of methyl lithium in ether (80 ml, 1.9 M solution) at ambient temperature under nitrogen was added portionwise over 0.5 hour finely divided 3,4-dihydro-7-hydroxy-4-(1-naphthyl)coumarin (7.52 g). The ether boiled during the addition and the solid material gradually dissolved. After the addition was complete the solution was boiled under reflux for 4 hours then cooled and poured into acid. The ether extract yielded 4-(2,4-dihydroxyphenyl)-2-methyl-4-(1-naphthyl)-2-butanol which was dissolved in glacial acetic acid (55 ml) and boiled under reflux overnight. The product was poured into water (200 ml) and extracted into ether. The ether extract was washed with water and aqueous sodium bicarbonate then dried (magnesium sulphate). Removal of the solvent gave the title compound (7.70 g) as a foam containing some ether.

PREPARATION 14

7-Cyanomethyloxy-2,2-dimethyl-4-(3-trifluoromethylphenyl)-chroman

Sodium hydride (0.93 g, 80% dispersion in oil) was added to a solution of 2,2-dimethyl-4-(3-trifluoromethylphenyl)chroman-7-ol (containing 1 mole of carbon tetrachloride of crystallisation) (7.5 g) in dimethylformamide (25 ml). Chloroacetonitrile (1.76 g) was added and the mixture heated at 60° C. for 3 hours. The solvent was removed under reduced pressure and the resulting oil was poured into water. The aqueous solution was extracted with ether and the etheeal extracts were dried (MgSO$_4$) and evaporated under reduced pressure to yield an oil. Chromatography on alumina with ether—petrol (40°–60° C.), 1:3 as eluate gave the title compound which crystallised on standing.

PREPARATION 15

2,2-Dimethyl-7-(2-hydroxyethyloxy)-4-(4-trifluoromethylphenyl) chroman tosylate (a)

2,2-Dimethyl-7-(2-hydroxyethyloxy)-4-(4-trifluoromethylphenyl) chroman

Sodium hydride (0.6 g, 80% dispersion in oil) was added to 2,2-dimethyl-4-(4-trifluoromethylphenyl) chroman-7-ol (containing 1 mole of carbon tetrachloride of crystallisation) (6 g) in dry toluene (20 ml) and the suspension was stirred and boiled under reflux for 30 minutes. Ethylbromoacetate (2.1 g) in toluene (5 ml) was added and the suspension boiled under reflux for a further 9 hours. The solvents were removed under reduced pressure and the residue was taken up in ether. The ethereal solution was washed with water and dried (MgSO$_4$). Removal of the solvent under reduced pressure gave an oil (5.4 g) which was identified by its spectrophotometric properties as 2,2-dimethyl-7-(carbethoxymethyleneoxy)-4-(4-trifluoromethylphenyl) chroman. Lithium aluminium hydride (0.2 g) was added to the above ester (1 g) in dry ether (30 ml) and the mixture boiled under reflux for 15 minutes. Water (1 ml), 1 M sodium hydroxide (1 ml) and further water (3 ml) were added and the suspension was extracted with ether (2×25 ml). The combined ethereal extracts were dried (MgSO$_4$) and evaporated under reduced pressure to give a clear oil (0.79g) which was identified by its spectrophotometric properties as the title compound.

(b)

2,2-Dimethyl-7-(2-hydroxyethyloxy)-4-(4-trifluoromethylphenyl-chroman tosylate p-Toluene-sulphonyl chloride (0.42 g) was added portionwise to a solution of 2,2-dimethyl-7-(2-hydroxyethyloxy)-4-(4-trifluoromethylphenyl) chroman (0.7 g) in pyridine (20 ml.) and the solution left at room temperature for 2 hours and then at 0° C. for 12 hours. The reaction mixture was poured onto ice, extracted with ether (2×100 ml.) and the ether extract dried (sodium sulphate). Removal of the solvent under reduced pressure gave an oil (0.65 g.) which had spectroscopic properties consistent within the title compound.

PREPARATION 16

2,2-Dimethyl-7-(2-dimethylaminoethoxy)-4(6-methoxy-2-naphthyl)-2H-chromene (a) Ethyl(6-methoxy-2-naphthoyl) acetate To a refluxing mixture of diethylcarbonate (71 g, 0.6 mole) and sodium hydride (44 g, 80% dispersion in oil) in benzene (400 ml) was added dropwise over 3 hours 6-methoxy-2-acetylnaphthalene (60 g, 0.3 mole) in benzene (600 ml). After refluxing for 1 hour water was added to the cooled reaction mixture to give the sodium salt of the β-keto ester. The crude product was dissolved in concentrated hydrochloric acid and extracted with ether (3×). The combined ether extracts were dried and removal of the solvent gave ethyl(6-methoxy-2-naphthoyl) acetate (61.0, 75%) as a dark coloured oil which partially decomposed to the starting ketone on attempted distillation.

(b) 7-Hydroxy-4(6-methoxy-2-naphthyl)coumarin

A stirred solution of ethyl(6-methoxy-2-naphthoyl) acetate (36 g, 0.132 mole), resorcinol (14.6 g, 0.132 mole) and phosphoryl chloride (32 ml) in benzene (200 ml) was refluxed for 3 hours. The reaction mixture was allowed to cool, poured into ice/water and filtered to give the crude product as a red solid. Recrystallisation from ethanol gave 7-hydroxy-4(6-methoxy-2-naphthyl)-coumarin (28.9 g, 69%) m.p. 223°-225° C.

(c) 2,2-Dimethyl-7-hydroxy-4(6-methoxy-2-naphthyl)-2H-chromene

To a solution of methyl lithium (100 ml, 1.9 M solution in ether) was added over 0.5 hour 7-hydroxy-4(6-methoxy-2-naphthyl)coumarin (6.5 g, 0.02 mole). The reaction mixture was stirred for 4 hours, acidified with dilute hydrochloric acid, and stirred for a further 0.5 hour. The organic layer was separated, washed with saturated sodium bicarbonate solution and dried. Removal of the solvent gave 2,2-dimethyl-7-hydroxy-4(6-methoxy-2-naphthyl)-2H-chromene (6.5 g, 96%) as a dark coloured oil which was used in the next reaction without further purification.

(d) 2,2-Dimethyl-7-(2-dimethylaminoethoxy)-4(6-methoxy-2-naphthyl)-2H-chromene

To a refluxing solution of 2,2-dimethyl-7-hydroxy-4(6-methoxy-2-naphthyl)-2H-chromene (6.4 g, 0.019 mole) and sodium hydride (1.4 g, 80% depression in oil) in toluene (150 ml) was added dropwise 2-dimethylaminoethyl chloride (2.7 g, 0.025 mole). After refluxing for 3 hours the solution was cooled and water added. The organic layer was separated and removal of the solvent gave a residue which dissolved in ether and extracted with dilute hydrochloric acid (3×). The combined acid extracts were basified with 40% sodium hydroxide solution and extracted with ether (3×). The combined ether extracts were dried and removal of the solvent gave a quantitative yield of 2,2-dimethyl-7-(2-dimethylaminoethoxy)-4(6-methoxy-2-naphthyl)-2H-chromene which was converted to the hydrochloride salt m.p. 96°-98° C.

PREPARATION 17

(a) 2-2-Dimethyl-4-(3-trifluoromethylphenyl)chroman-7-yl 2-methyl carbonate

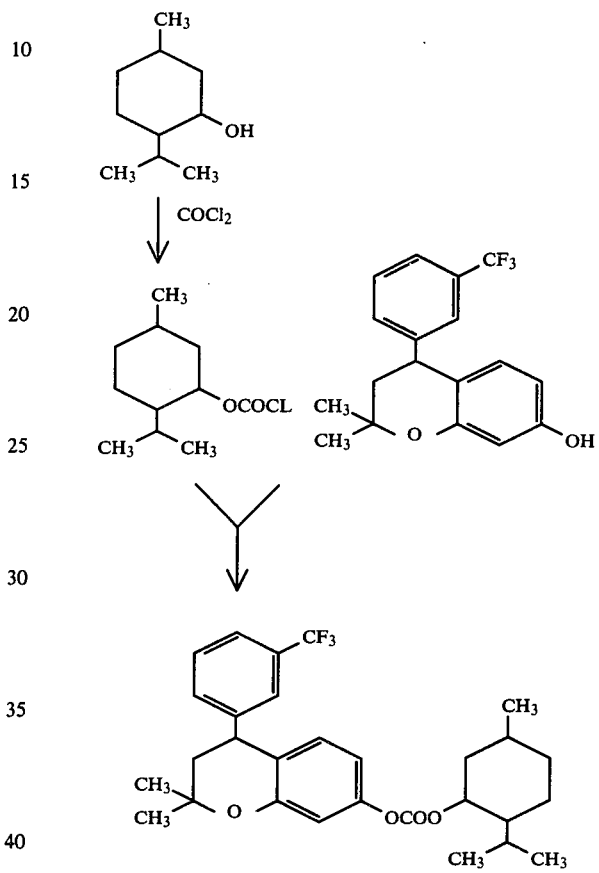

1-Methanol (14 g) in ether (50 ml) was added dropwise to phosgene in toluene (12%, 200 ml). The solution was allowed to stand overnight, then the solvent and excess phosgene evaporated, yielding an oil (20 g) which was used directly. [I.r. shows C=O band at 1740cm$^{-1}$].

2,2-Dimethyl-4-(3-trifluoromethylphenyl)chroman-7-ol (24 g) in ether (200 ml) was added drop-wise to 1-menthyloxycarbonyl chloride (20 g) in ether (100 ml). The mixture was stirred and pyridine (10 ml) added slowly. After 10 minutes a solid separated. The mixture was stirred for 2 hours, ether (200 ml) added and the solid filtered off and washed with ether. Evaporation of the combined ether layers gave an oil (50 g) which solidified, m.p. 109°-119° C. (α (CHCl₃)= −32.5°). T.l.c. (silica gel/chloroform) showed a small trace of starting phenol.

The mixture was resolved by fractional crystallisation from ethanol. A typical separation is illustrated below; the solvent is ethanol, the solvent for the polarimeter is chloroform.

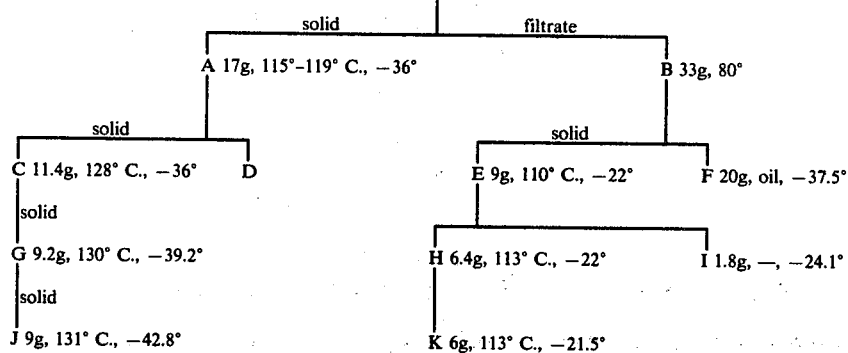

(b)
(−)-2,2-Dimethyl-4-(3-trifluoromethylphenyl)chroman-7-ol and
(+)-2,2-dimethyl-4-(3-trifluoromethylphenyl)chroman-7-ol

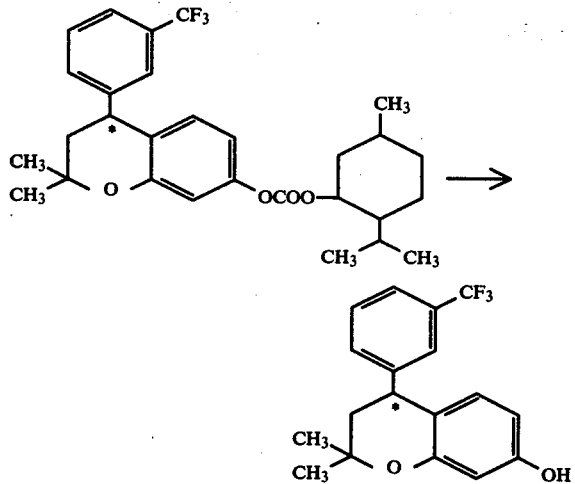

2,2-Dimethyl-4-(3-trifluoromethylphenyl)chroman-7-yl 2-menthyl carbonate (α=−21.5°, m.p. 113° C.) (6 g) was heated to 200° in a wide necked conical flask. The carbonate decomposed, the reaction being followed by t.l.c., giving a dark brown glass (3.8 g, α=+17°). The compound was not purified but used directly.

Similarly, the other diastereomer (α−−42.5°, m.p. 131° C.) was decomposed to give a dark brown glass, α−−16.4°. The n.m.r. spectra were identical with authentic chromanol.

PREPARATION 18

2,2-Dimethyl-4-(2-naphthyl)-7-[2-(1-piperidino)ethoxy]-2H-chromene (a) 7-Hydroxy-4-(2-naphthyl)coumarin A mixture of resorcinol (11.0 g, 0.1 mole) and ethyl 2-naphthoylacetate (24.2 g, 0.1 mole) in concentrated sulphuric acid (50 ml) was stirred at room temperature for 5 days then poured into water to give a yellow gum. The gum was washed several times with water then dissolved in ethanol and diluted with water to give 7-hydroxy-4-(2-naphthyl)coumarin as a fine pale brown precipitate in 26% yield.

(b) 2,2-Dimethyl-4-(2-naphthyl)-2H-chromen-7-ol

To a stirred solution of methyl lithium (0.04 mole, 20 ml of a 1.9 M solution in ether) under nitrogen at ambient temperature was added portionwise 7-hydroxy-4-(2-naphthyl)coumarin (2.89 g, 0.01 mole). After 5 hours the solution was decomposed with acid to give 2,2-dimethyl-4-(2-naphthyl)-2H-chromen-7-ol as a crude dark brown foam (2 g) which was used without further purification.

(c)
2,2-Dimethyl-4-(2-naphthyl)-7-[2-(1-piperidino)ethoxy]-2H-chromene

A mixture of 2,2-dimethyl-4-(2-naphthyl)-2H-chromen-7-ol (2.0 g), N-2-chloroethylpiperidino hydrochloride (1.2 g), anhydrous potassium carbonate (2.8 g) and potassium iodide (0.35 g) in anhydrous acetone (16 ml) was stirred under reflux for 4 hours.

The solution was filtered hot and the acetone removed in vacuo. The residue was partitioned between ether—5 N hydrochloric acid and the organic layer was extracted with two further portio of acid. The combined acid extracts were basified and extracted into ether to give a brown gum (2.02 g) which was purified by chromatography on alumina in 12% ether—88% light petroleum (b.p. 60°-80°) to give the title compound (1.67 g, 61%) as a colourless oil. A portion was converted to the hydrochloride salt, m.p. 226°-229° C. (ex acetone).

PREPARATION 19

(a)
7-[2-(N-benzyl-N-methylamino)ethoxy]-2,2-dimethyl-4-(2-naphthyl)-2H-chromene Reaction of N-benzyl-N-(2-chloroethyl)methylamine hydrochloride with 2,2-dimethyl-4-(2-naphthyl)-2H-chromen-7-ol by an analogous method to that described in Preparation 18 (c) gave the title compound (49%) as a colourless oil, The hydrochloride salt had m.p. 112°-115° C. decomposed.

(b)
7-(2-Diethylaminoethoxy)-2,2-dimethyl-4-(2-naphthyl)-2 H-chromene

Reaction of 2-diethylaminoethylchloride hydrochloride with 2,2-dimethyl-4-(2-naphthyl)-2H-chromen-7-ol by an analogous method to that described in Preparation 18 (c) gave the title compound as a colourless oil in 49% yield.

We claim:

1. A compound of the formula

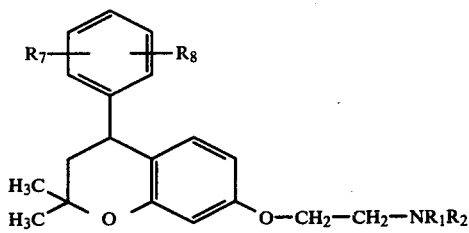

or a pharmaceutically acceptable acid addition salt thereof wherein $R_1$ is hydrogen, methyl or ethyl; $R_2$ is methyl or ethyl; $R_7$ is fluoro, chloro, methyl, methoxyl or trifluoromethyl; and $R_8$ is fluoro or chloro.

2. The hydrochloride salt of a compound of the formula

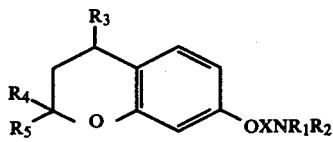

wherein X is $CH_2CH_2$; and $R_1$ and $R_2$ are each methyl; $R_3$ is 4-chloro-3-trifluoromethylphenyl; and $R_4$ and $R_5$ are each methyl.

3. The hydrochloride salt of a compound of the formula

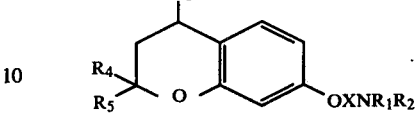

wherein X is $CH_2CH_2$; and $R_1$ and $R_2$ are each methyl; $R_3$ is 4-fluoro-3-trifluoromethylphenyl; and $R_4$ and $R_5$ are each methyl.

4. The hydrochloride salt of a compound of the formula

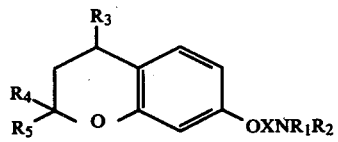

wherein X is $CH_2CH_2$; $R_1$ and $R_2$ are each methyl; $R_3$ is 3,5-bis-trifluoromethylphenyl; and $R_4$ and $R_5$ are each methyl.

* * * * *